United States Patent
Jadav et al.

(10) Patent No.: US 8,471,016 B2
(45) Date of Patent: Jun. 25, 2013

(54) PROCESS FOR THE PREPARATION OF CHIRAL BETA AMINO CARBOXAMIDE DERIVATIVES

(75) Inventors: Kanaksinh Jesingbhai Jadav, Baroda (IN); Rutvij Manharlal Bhatt, Baroda (IN); Kamleshkumar Naranbhai Borkhataria, Baroda (IN); Trinadha Rao Chitturi, Baroda (IN); Rajamannar Thennati, Baroda (IN)

(73) Assignee: Sun Pharmaceutical Industries Ltd., Andheri-East Mumbai ( * ) Notice: Subject to any disclaimer, the term of this patent is extended or adjusted under 35 U.S.C. 154(b) by 0 days.

(21) Appl. No.: 13/642,872

(22) PCT Filed: Apr. 28, 2011

(86) PCT No.: PCT/IN2011/000289
§ 371 (c)(1),
(2), (4) Date: Oct. 23, 2012

(87) PCT Pub. No.: WO2011/135586
PCT Pub. Date: Nov. 3, 2011

(65) Prior Publication Data
US 2013/0041150 A1    Feb. 14, 2013

(30) Foreign Application Priority Data
Apr. 28, 2010   (IN) .......................... 1358/MUM/2010

(51) Int. Cl.
*C07D 487/04*   (2006.01)
*C07C 227/18*   (2006.01)
*C07C 229/34*   (2006.01)

(52) U.S. Cl.
USPC ........................................ 544/350; 562/449

(58) Field of Classification Search
USPC .............................. 560/37; 544/350; 562/449
See application file for complete search history.

(56) References Cited

U.S. PATENT DOCUMENTS

| 6,699,871 B2 | 3/2004 | Edmondson et al. |
| 2008/0058522 A1 | 3/2008 | Xiao et al. |
| 2009/0192326 A1 | 7/2009 | Perlman et al. |

FOREIGN PATENT DOCUMENTS

WO   WO-2004/085661 A2   10/2004

*Primary Examiner* — Kristin Bianchi
(74) *Attorney, Agent, or Firm* — Schwegman Lundberg & Woessner, P.A.

(57) ABSTRACT

The present invention provides a process for preparing a compound of formula (I), or a pharmaceutically acceptable salt thereof, having the R-configuration, of formula (IA), or S-configuration of formula (IB), selectively over the other enantiomer.

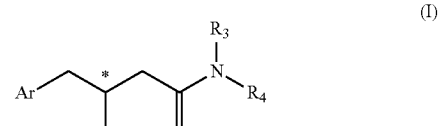

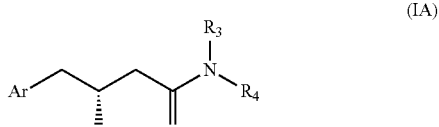

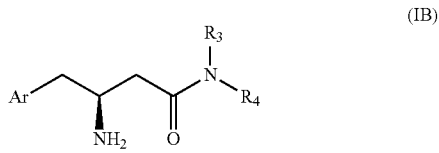

17 Claims, No Drawings

PROCESS FOR THE PREPARATION OF CHIRAL BETA AMINO CARBOXAMIDE DERIVATIVES

RELATED APPLICATIONS

This application is a national stage application under 35 U.S.C. §371 of PCT/IN2011/000289, filed Apr. 28, 2011, and published as WO 2011/135586 A2 on Nov. 3, 2011, which claims the benefit of Indian Patent Application No. 1358/MUM/2010 filed on Apr. 28, 2010 which applications and publication are incorporated by reference as if reproduced herein and made a part hereof in their entirety, and the benefit of priority of each of which is claimed herein.

FIELD OF INVENTION

The present invention relates to a process for the efficient preparation of enantiomerically enriched beta-amino carboxamide derivatives. More particularly the present invention relates to a process for the preparation of enantiomerically enriched beta-amino carboxamide inhibitors of dipeptidyl peptidase-IV which are useful for the treatment of type 2 diabetes.

BACKGROUND OF THE INVENTION

Chiral beta-amino carboxamide compounds are frequent constituents of drug candidates, and are also useful in the asymmetric synthesis of biologically active molecules.

The most utilized route to enantiomerically enriched or enantiomerically pure amines to date is optical resolution of the corresponding racemic mixture of the amine. Conventionally, the optical resolution is effected via diastereomeric salts. An alternative to optical resolution via diastereomeric derivatives is biocatalytic kinetic resolution. The disadvantage of optical resolution is a limitation of the theoretical yield to a maximum of 50% from the racemate. The undesired enantiomer has to be either disposed off, or converted back to the racemate and recycled into the production process. The additional working steps for the recycling of the undesired enantiomer are associated with considerable cost and effort.

These disadvantages, which apply in principle to all optical resolution strategies can be avoided by an asymmetric synthesis using prochiral starting compounds. The known asymmetric syntheses using transition metal catalysts, however, often do not achieve the required enantioselectivity. Besides these catalysts, which are generally coordinated with chiral ligands, are often difficult to recover from the reaction mixtures. Furthermore, the use of transition metal catalysts can result in traces of transition metals in the resulting product which is undesirable for pharmaceutical applications.

In the synthesis of chiral amines by use of biocatalysts, product isolation and the recovery and re-use of the enzyme is sometimes associated with difficulties. Other associated drawbacks of biocatalytic reactions include factors such as solubility issues (due to limitations on the type of solvents that can be used), extensive downstream processing operations, and high reaction volumes that may be sometimes required.

Sitagliptin, 7-[(3R)-3-amino-1-oxo-4-(2,4,5trifluorophenyl)butyl]-5,6,7,8-tetrahydro-3-(trifluoromethyl)-1,2,4-triazolo[4,3-a]pyrazine, a chiral beta-amino carboxamide having the following chemical structure, is an inhibitor of dipeptidyl peptidase-IV.

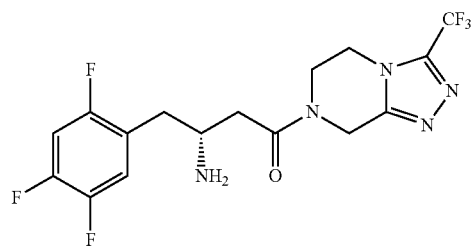 [SMILES: N[C@@H](CC(=O)N1CCn2c(nnc2C(F)(F)F)C1)Cc1cc(F)c(F)cc1F]

Sitagliptin is currently marketed as its phosphate salt in the United States under the trade name JANUVIA™. JANUVIA™ is indicated to improve glycemic control in patients with type 2 diabetes mellitus.

U.S. Pat. No. 6,699,871 (Assigned to Merck and Company), discloses a process for preparing sitagliptin. The process disclosed in this patent is very tedious involving several steps and is not suitable for commercial scale manufacture.

WO 2004/085661 (Assigned to Merck and Company) discloses a process for preparing sitagliptin in which (S)-phenylglycine amide is used as a chiral auxiliary to form an intermediate that subsequently provides the desired enantiomer of the amine.

US Patent Application 2008/0058522 (Merck & Company) discloses a process for preparation of enatiomerically enriched beta-amino acid or derivatives by enantioselective hydrogenation of an amine-unprotected prochiral beta-amino acrylic acid or derivative thereof in presence of rhodium metal complexed with a chiral phosphorous ligand. Synthesis of sitagliptin has been exemplified by this method.

US Patent Application 2009/0192326 discloses preparation of sitagliptin by using N-protected 3-amino-4-(2,4,5-trifluorophenyl)butanoic acid alkyl ester as key intermediate, which in turn is obtained by asymmetric reduction of 3-amino-4-(2,4,5-trifluorophenyl)but-2-enoic acid with a rhodium catalyst coordinated with chiral phosphorous ligands.

The processes reported for preparing sitagliptin as mentioned vide supra suffer from drawbacks such as involving use of expensive reagents like platinum oxide or rhodium oxide or metal catalysts with chiral ligands. Some processes require protection and deprotection steps, while some use flammable and expensive solvents. There is therefore a need for a simple, efficient and commercially viable process which does not use expensive reagents or hazardous solvents and for the preparation of the compound of formula I with high chiral purity to the extent of at least 99.9%.

We have now found out that we can achieve with high chiral purity to the extent of at least 99.9% the compound of formula IA-1 through hydrogenolysis of the compound of formula IVA-1, which in turn is obtained by the reaction of compound of formula IIA-1 with a compound of formula IIIA.

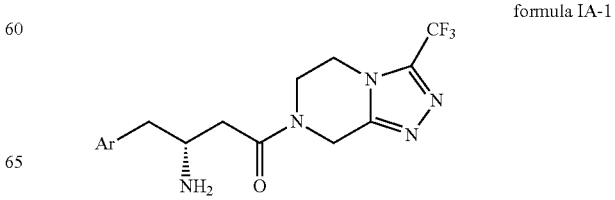

formula IA-1

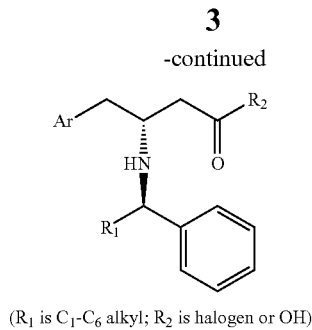

formula IIA-1

($R_1$ is $C_1$-$C_6$ alkyl; $R_2$ is halogen or OH)

formula IIIA formula IVA-1

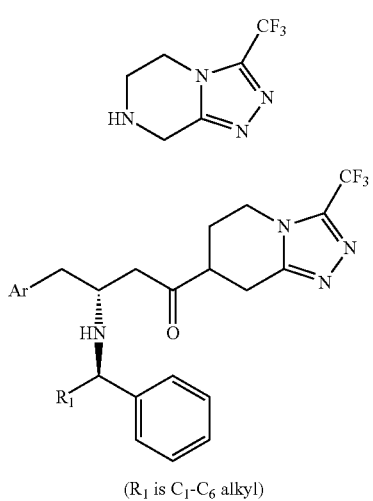

($R_1$ is $C_1$-$C_6$ alkyl)

SUMMARY OF THE INVENTION

The present invention provides a process for preparing a compound of formula I, or a pharmaceutically acceptable salt thereof, having the R-configuration, of formula IA, or S-configuration of formula IB, selectively over the other enantiomer formula I

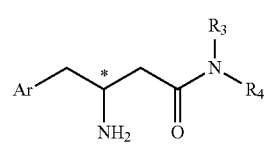

formula IA

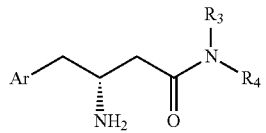

formula IB

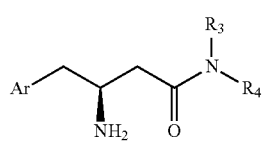

wherein,

Ar is selected from aryl or heteroaryl which is unsubstituted or substituted with one to five substituents independently selected from the group consisting of halogen, $C_{1-8}$ alkyl, hydroxyl, cyano, nitro, alkoxy, haloalkoxy;

$R_3$ and $R_4$ are each independently hydrogen, $C_{1-8}$ alkyl, aryl, or alkylaryl or arylalkyl with a proviso that it is not 1-arylalkyl; or $R_3$ and $R_4$ together with the nitrogen atom to which they are attached to form a 4- to 7-membered heterocyclic ring system optionally containing an additional heteroatom selected from O, S, N, said heterocyclic ring being unsubstituted or substituted with one to three substituents independently selected from oxo, hydroxy, halogen, $C_{1-4}$ alkoxy, and $C_{1-4}$ alkyl wherein alkyl and alkoxy are unsubstituted or substituted with one or more halogens; and said heterocyclic ring system being optionally fused with a 5 or 6-membered saturated or aromatic carbocyclic ring system or a 5 or 6-membered saturated or aromatic heterocyclic ring system containing one or two hetero atoms selected from O, S, and N, said fused ring system being unsubstituted or substituted with one or two substituents selected from hydroxy, amino, halo, $C_{1-4}$ alkyl, $C_{1-4}$ alkoxy, and haloalkyl; comprising a. condensation of a compound of formula IIA, or its enantiomer of formula IIB, with a compound of formula III, or a salt thereof, to form a compound of formula IVA, or its enantiomer of formula IVB respectively;

formula IIA

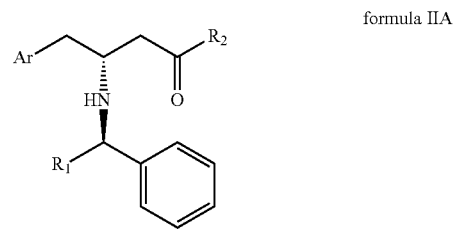

formula IIB ($R_1$ is $C_1$-$C_6$ alkyl; $R_2$ is halogen or OH)

formula III formula IVA

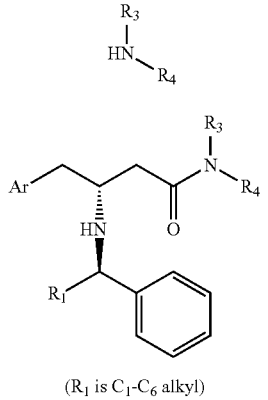

($R_1$ is $C_1$-$C_6$ alkyl)

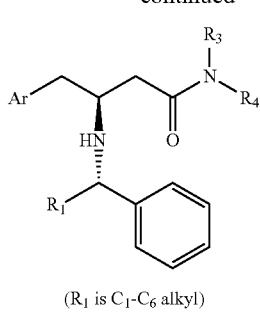

formula IVB ($R_1$ is $C_1$-$C_6$ alkyl)

b. hydrogenolysis of the compound of formula IVA or its enantiomer a compound of formula IVB to the corresponding compound of formula IA or compound of formula IB, respectively; and c. optionally converting the compound of formula IA or IB to a pharmaceutically acceptable salt.

DESCRIPTION OF THE INVENTION

The process of the present invention provides compounds of structural formula I with high optical purity, typically >99%. In one embodiment, compounds of formula I are obtained with an optical purity in excess of 99.9%.

The alkyl groups specified above are intended to include those alkyl groups of the designated length in either a straight or branched configuration. Exemplary of such alkyl groups are methyl, ethyl, propyl, isopropyl, butyl, sec-butyl, tertiary-butyl, n-pentyl, isopentyl, hexyl, isohexyl, and the like. The alkyl groups are unsubstituted or substituted with one to three groups independently selected from the group consisting of halogen, hydroxy, carboxy, aminocarbonyl, amino, $C_{1-4}$ alkoxy, and $C_{1-4}$ alkylthio.

The term "cycloalkyl" is intended to mean cyclic rings of alkanes of five to twelve total carbon atoms, or any number within this range (i.e., cyclopentyl, cyclohexyl, cycloheptyl, etc).

The term "halogen" is intended to include the halogen atoms fluorine, chlorine, bromine, and iodine.

The term "aryl" includes phenyl and naphthyl. "Aryl" is unsubstituted or substituted with one to five substituents independently selected from fluoro, hydroxy, trifluoromethyl, amino, $C_{1-4}$ alkyl, and $C_{1-4}$ alkoxy.

The term "heteroaryl" means a 5- or 6-membered aromatic heterocycle that contains at least one ring heteroatom selected from O, S and N. Heteroaryls also include heteroaryls fused to other kinds of rings, such as aryls, cycloalkyls and heterocycles. Examples of heteroaryls groups include, but are not limited to, pyrrolyl, isoxazolyl, isothiazolyl, pyrazolyl, pyridinyl, oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, isobenzylfuranyl, benzimidazolyl, benzofuranyl, benzothienyl, quinolyl, indolyl, isoquinolyl, and dibenzofuranyl. "Heteroaryl" is unsubstituted or substituted with one to five substituents independently selected from fluoro, hydroxy, trifluoromethyl, amino, $C_{1-4}$ alkyl, and $C_{1-4}$ alkoxy.

In one embodiment the present invention provides a process for preparing a compound of formula I, or a pharmaceutically acceptable salt thereof, having the R-configuration, of formula IA, or S-configuration of formula IB, selectively over the other enantiomer

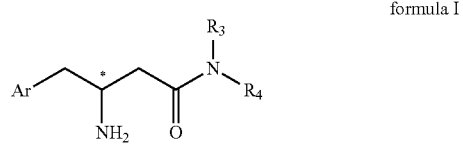

formula I

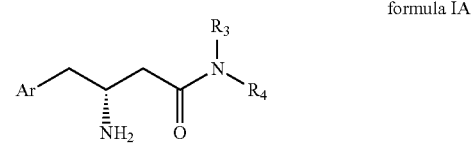

formula IA

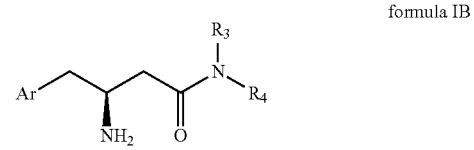

formula IB wherein,

Ar is selected from aryl or heteroaryl which is unsubstituted or substituted with one to five substituents independently selected from the group consisting of halogen, $C_{1-8}$ alkyl, hydroxyl, cyano, nitro, alkoxy, haloalkoxy;

$R_3$ and $R_4$ are each independently hydrogen, $C_{1-8}$ alkyl, aryl, or alkylaryl or arylalkyl with a proviso that it is not 1-arylalkyl; or $R_3$ and $R_4$ together with the nitrogen atom to which they are attached to form a 4- to 7-membered heterocyclic ring system optionally containing an additional heteroatom selected from O, S, N, said heterocyclic ring being unsubstituted or substituted with one to three substituents independently selected from oxo, hydroxy, halogen, $C_{1-4}$ alkoxy, and $C_{1-4}$ alkyl wherein alkyl and alkoxy are unsubstituted or substituted with one or more halogens; and said heterocyclic ring system being optionally fused with a 5 or 6-membered saturated or aromatic carbocyclic ring system or a 5 or 6-membered saturated or aromatic heterocyclic ring system containing one or two hetero atoms selected from O, S, and N, said fused ring system being unsubstituted or substituted with one or two substituents selected from hydroxy, amino, halo, $C_{1-4}$ alkyl, $C_{1-4}$ alkoxy, and haloalkyl; comprising a. condensation of a compound of formula IIA, or its enantiomer of formula IIB, with a compound of formula III, or a salt thereof, to form a compound of formula IVA, or its enantiomer of formula IVB respectively;

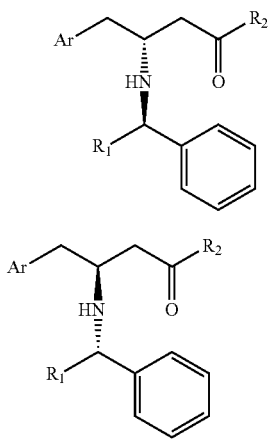

formula IIA formula IIB ($R_1$ is $C_1$-$C_6$ alkyl; $R_2$ is halogen or OH)

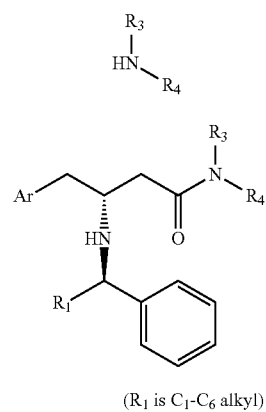

formula III formula IVA ($R_1$ is $C_1$-$C_6$ alkyl)

formula IVB

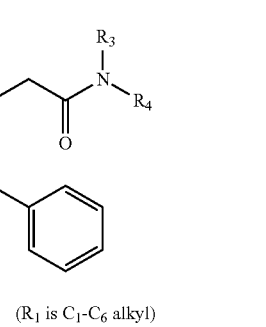

($R_1$ is $C_1$-$C_6$ alkyl)

b. hydrogenolysis of the compound of formula IVA or its enantiomer a compound of formula IVB to the corresponding compound of formula IA or compound of formula IB, respectively; and
c. optionally converting the compound of formula IA or IB to a pharmaceutically acceptable salt.

The amide coupling reaction of compound of formula IIA or its enantiomer, IIB with a compound of formula III is carried out in the presence of a coupling agent in a suitable solvent. The coupling agent is selected from the group consisting of benzotriazole-1-yl-oxy-tris(dimethylamino)phosphonium hexafluorophosphate (BOP), N,N'-dicyclohexylcarbodiimide (DCC), N-(3-dimethylaminopropyl)-N-ethylcarbodiimide (EDC), isobutyl chloroformate and pivaloyl chloride optionally with use of catalytic 1-hydroxybenzotriazole (HOBt), in a solvent.

Suitable solvents for the amide coupling reaction may be selected from the group consisting of THF, acetonitrile, dichloromethane, N,N-dimethylformamide, N,N-dimethylacetamide, ethyl acetate and toluene.

The compound of formula IIA or IIB ($R_2$=halogen) can be prepared from the corresponding acid ($R_2$=halogen) by reaction with a halogenating agent.

The hydrogenolysis of the compound of formula IVA or its enantiomer IVB to the corresponding compound of formula IA or formula IB respectively may be carried out using a hydrogenation catalyst in a solvent. The hydrogenation catalyst is preferably 5% to 10% palladium on charcoal. The solvent may be selected form a protic solvent selected from the group consisting of water, methanol, ethanol, isopropanol or mixtures thereof, preferably containing 1 to 5 molar equivalents of an acid such as acetic acid, hydrochloric acid or phosphoric.

In one embodiment the present invention provides a process for preparing a compound of formula IA-1, or a pharmaceutically acceptable salt thereof, with an optical purity in excess of 99.9%, formula IA-1

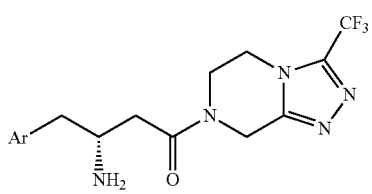

wherein Ar is phenyl which is unsubstituted or substituted with one to five substituents independently selected from the group consisting of halogen, $C_{1-8}$ alkyl, hydroxyl, cyano, nitro, alkoxy, haloalkoxy; comprising
a. condensation of a compound of formula IIA-1 with 3-(trifluoromethyl)-5,6,7,8-tetrahydro[1,2,4]triazolo[4,3-[alpha]]pyrazine, a compound of formula IIIA or salt thereof to form a compound of formula IVA-1;

formula IIA-1

($R_1$ is $C_1$-$C_6$ alkyl; $R_2$ is halogen or OH)

formula IIIA formula IVA-1

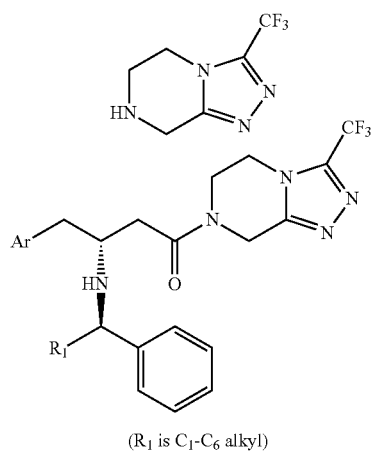

($R_1$ is $C_1$-$C_6$ alkyl)

b. hydrogenolysis of the compound of formula IVA-1 to compound of formula IA-1; and c. optionally converting the compound of formula IA-1 to pharmaceutically acceptable salt.

In one preferred embodiment the present invention provides a process for preparing compound of formula IA-1, wherein Ar is 2,4,5-trifluorophenyl viz.7-[(3R)-3-amino-1-oxo-4-(2,4,5trifluorophenyl)butyl]-5,6,7,8-tetrahydro-3-(trifluoromethyl)-1,2,4-triazolo[4,3-a]pyrazine phosphate, i.e. Sitagliptin phosphate with a chiral purity of 100%.

In one embodiment the present invention provides novel compounds of formula IIA-1 wherein Ar is phenyl which is unsubstituted or substituted with one to five substituents independently selected from the group consisting of halogen, $C_{1-8}$ alkyl, hydroxyl, cyano, nitro, alkoxy, haloalkoxy, $R_1$ is $C_1$-$C_6$ alkyl and $R_2$ is OH.

formula IIA-1

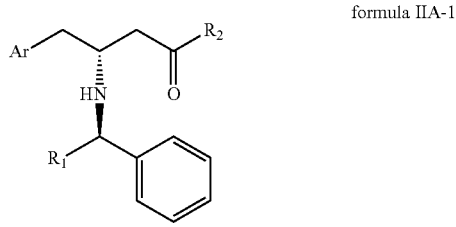

In one embodiment Ar is phenyl substituted with halogen, preferably fluorine, $R_1$ is $C_1$-$C_6$ alkyl and $R_2$ is OH.

In one embodiment Ar is selected from 2,4,5-trifluorophenyl, 2,4-difluorophenyl 2,5-difluorophenyl, and 3,4-difluorophenyl and $R_1$ is $C_1$-$C_6$ alkyl and $R_2$ is OH.

In one of preferred embodiment Ar is 2,4,5-trifluorophenyl, $R_1$ is methyl and $R_2$ is OH.

In one embodiment the present invention provides a process for preparing the compound of formula IIA-1, wherein Ar is 2,4,5-trifluorophenyl; $R_1$ is $C_1$-$C_6$ alkyl and $R_2$ is OH comprising, a. hydrogenating the compound of formula V in presence of a hydrogenation catalyst in a solvent to obtain a compound of formula VI;

formula V

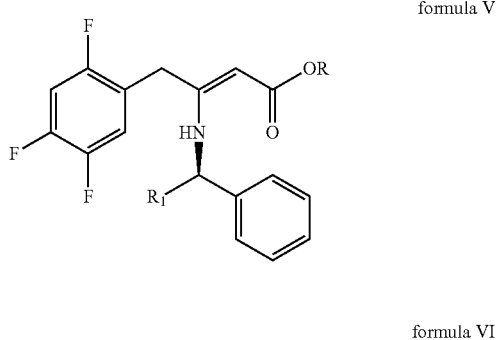

formula VI

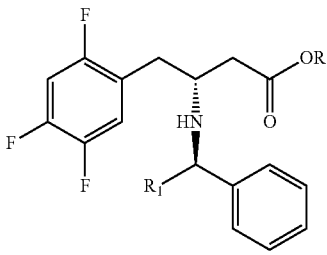

b. optionally converting the compound of formula VI to an acid addition salt; and c. hydrolyzing the compound of formula VI, or a salt thereof.

The compound of formula V is hydrogenated to the compound of formula VI using catalyst selected from the group consisting of Raney-Ni, platinum oxide or platinum on carbon. Preferably platinum on carbon is used as a catalyst. The hydrogenation may be carried out at temperature in the range of 0° C. to 100° C., preferably at 25-40° C. The hydrogenation is carried out at a pressure in the range of 1 to 10 atmospheres, preferably at 3 to 5 atmospheres. The hydrogenation may be carried out in presence or absence of a solvent Suitable solvents for hydrogenation include toluene, tetrahydrofuran, methanol, ethanol and isopropanol.

The examples that follow do not limit the scope of the present invention and are included as illustrations:

EXAMPLES

Example 1 tert-Butyl 3-[[(1R)-1-phenylethyl]amino]-4-(2,4,5-trifluorophenyl)-but-2-enoate [B]

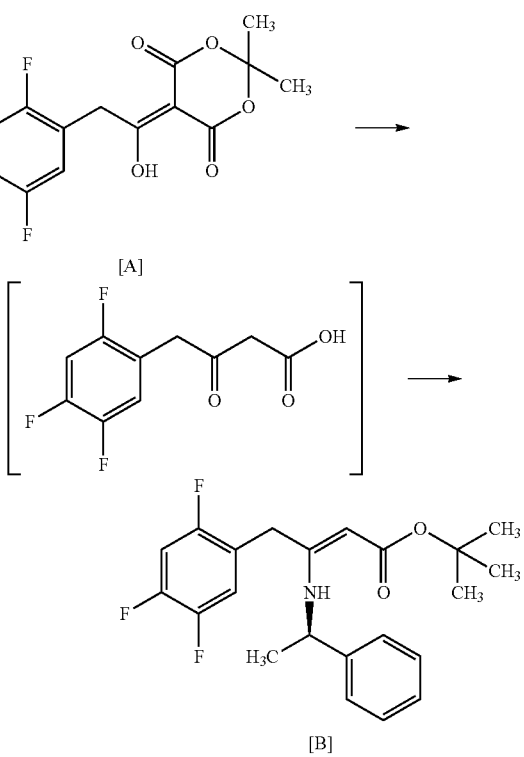

A mixture of 5-[1-hydroxy-2-(2,4,5-trifluorophenyl)ethylidene]-2,2-dimethyl-1,3-dioxane-4,6-dione [A] (50 g, 0.158 mol) in tert-butanol (250 ml) was heated to reflux (82±2° C.) for 1 hr and then (R)-(+)-α-methylbenzenamine (21 g, 0.173 mol) and acetic acid (9 ml, 0.157 mol) was added. The mixture was stirred at 30±2° C. for 8 hours, concentrated and degassed under reduced pressure. To the residue was added a mixture of methanol-water (3:1, 100 ml), stirred, filtered the solid and dried to obtain 51.9 g (83% yield) of the titled compound, m.p. 76° C.; purity by HPLC, 98.8%.

¹H NMR (400 MHz, CDCl₃): δ 1.45 (d, 3H), 1.50 (s, 9H), 3.15 (d, 1H), 3.40 (d, 1H), 4.32 (s, 1H), 4.40-4.44 (m, 1H), 6.80-6.88 (m, 1H), 6.92-7.00 (m, 1H), 7.15-7.33 (m, 5H), 8.89 (d, 1H).

¹³C NMR (200 MHz, CDCl₃): δ 25.76, 29.27 (3C), 31.47 (d, $J_{C-F}$=2.6 Hz), 53.38, 79.23, 87.83, 105.94 (dd, $J_{C-F}$=28.3 Hz, 20.9 Hz), 118.61 (dd, $J_{C-F}$=19.8 Hz, 4.4 Hz), 120.78 (ddd, $J_{C-F}$=17.6 Hz, 5.4 Hz, 4.2 Hz), 125.95 (2C), 127.77, 129.40 (2C), 145.54, 160.17, 171.05.

Using similar procedure as described in Example 1, the following compounds are prepared, tert-butyl 3-[[(1R)-1-phenylethyl]amino]-4-(2,4-difluorophenyl)but-2-enoate, tert-butyl 3-[[(1R)-1-phenylethyl]amino]-4-(2,5-difluorophenyl)but-2-enoate, tert-butyl 3-[[(1R)-1-phenylethyl]amino]-4-(3,4-difluorophenyl)but-2-enoate.

Example 2 tert-Butyl (3R)-3-[[(1R)-1-phenylethyl]amino]-4-(2,4,5-trifluorophenyl)butanoate maleate salt [C]

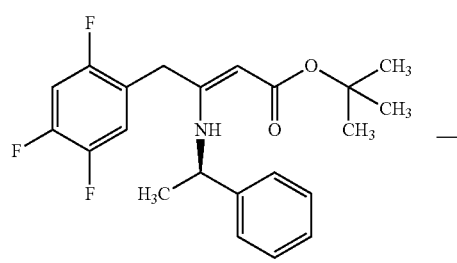

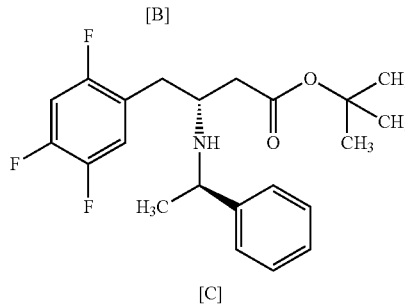

[C]

tert-Butyl 3-[[(1R)-1-phenylethyl]amino]-4-(2,4,5-trifluorophenyl)but-2-enoate [B] (300 g 0.766) was dissolved in 2-propanol (2400 ml) and hydrogenated in presence of 5% platinum on charcoal at 35° C. under hydrogen pressure of 4.0 kg/cm². After completion of hydrogenation, the catalyst was filtered and to the filtrate was added maleic acid (90 g, 0.775 mol) to obtain product as a crystalline maleate salt. The solid was filtered, suspended in 2-propanol (1200 ml) and refluxed for 1 hour. Cooled to ambient temperature, filtered and dried to yield the titled product[C], m.p. 160° C., purity by HPLC 99.7%, content of diastereomer (3S)-3-[[(1R)-1-phenylethyl]amino]-4-(2,4,5-trifluorophenyl)butanoate maleate 0.05%.

¹H NMR (400 MHz, CDCl₃): δ 1.38 (s, 9H), 1.77 (d, 3H), 2.52 (dd, 1H), 2.83 (dd, 1H), 2.94 (dd, 1H), 3.07 (dd, 1H), 3.50-3.57 (m, 1H), 4.51 (q, 1H), 6.31 (s, 2H), 6.79-6.90 (m, 2H), 7.41-7.49 (m, 3H), 7.51-7.53 (m, 2H).

¹³C NMR (200 MHz, CDCl₃): δ 20.97, 28.51 (3C), 32.09, 36.22, 53.76, 58.66, 83.02, 106.28 (dd, $J_{C-F}$=28.1 Hz, 20.7 Hz), 119.25-120.29 (2C), 28.47 (2C), 130.18 (2C), 130.25, 136.73 (2C), 136.91, 170.23, 170.61 (2C).

Using similar procedure as described in Example 2, the following compounds are prepared, (3R)-3-[[(1R)-1-phenylethyl]amino]-4-(2,4-difluorophenyl)butanoate, (3R)-3-[[(1R)-1-phenylethyl]amino]-4-(2,5-difluorophenyl)butanoate, (3R)-3-[[(1R)-1-phenylethyl]amino]-4-(3,4-difluorophenyl)butanoate.

Example 3

(3R)-3-[[(1R)-1-phenylethyl]amino]-4-(2,4,5-trifluorophenyl)-butanoic acid [D]

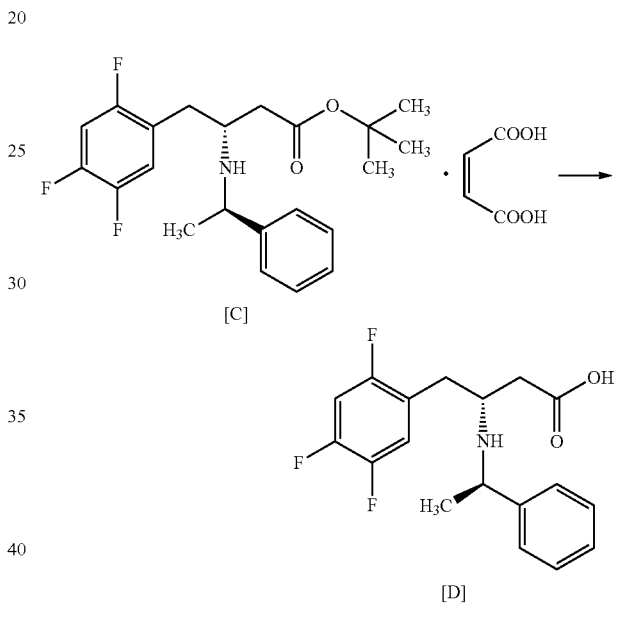

tert-Butyl (3R)-3-[[(1R)-1-phenylethyl]amino]-4-(2,4,5-trifluorophenyl)-butanoate maleate salt [C] (50 g) was stirred in a mixture of water (250 ml) and conc. sulfuric acid (16 ml) at 70° C. for 2 hours. The pH was adjusted to 4.2±0.2 with aqueous sodium hydroxide solution and then to 7.0±0.2 with ammonia solution. Filtered the solid and purified by suspending in water at 25±5° C. for 1 hr. Filtered and dried to yield 31.3 g (94.5% theoretical yield) of titled product [D], m.p. 144° C., purity by HPLC: 98.8%.

¹H NMR (400 MHz, CDCl₃): δ 1.58 (d, 3H), 2.24 (dd, 1H), 2.52 (dd, 1H), 2.79 (dd, 1H), 2.97 (dd, 1H), 3.12-3.18 (m, 1H), 4.09 (q, 1H), 6.80-6.90 (m, 2H), 7.28-7.38 (m, 5H).

¹³C NMR (200 MHz, CDCl₃): δ 22.11, 31.74, 34.85, 53.87, 56.46, 106.10 (dd, $J_{C-F}$=28.2 Hz, 20.7 Hz), 119.93 (dd, $J_{C-F}$=19.2 Hz, 5.7 Hz), 120.52-121.07, 127.75 (2C), 129.41, 129.85 (2C), 139.48, 176.00.

Using similar procedure described in Example 3, the following compounds are prepared, (3R)-3-[[(1R)-1-phenylethyl]amino]-4-(2,4-difluorophenyl)butanoic acid, (3R)-3-[[(1R)-1-phenylethyl]amino]-4-(2,5-difluorophenyl)butanoic acid, (3R)-3-[[(1R)-1-phenylethyl]amino]-4-(3,4-difluorophenyl) butanoic acid.

Example 4

(2R)-4-oxo-N-[(1R)-1-phenylethyl]-1-(2,4,5-trifluorophenyl)-4-[3-(trifluoromethyl)-5,6-dihydro[1,2,4] triazolo[4,3-a]pyrazin-7(8H)-yl]butan-2-amine [F]

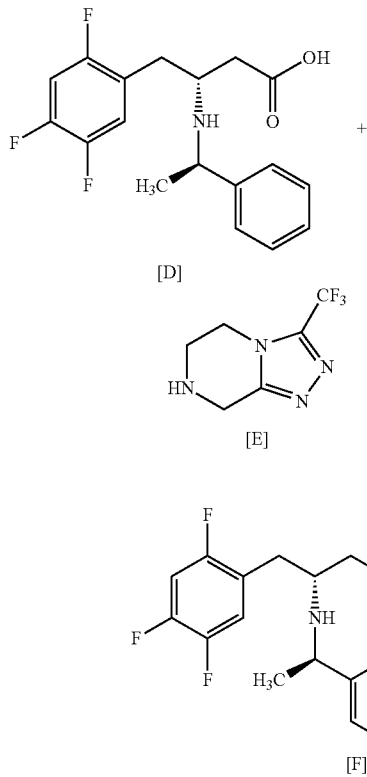

To a stirred solution of (3R)-3-[[(1R)-1-phenylethyl] amino]-4-(2,4,5-trifluorophenyl)butanoic acid [D] (25 g, 0.074 mol) and triethylamine (26 ml, 0.187 mol) in dichloromethane (250 ml) at 3±2° C. was added gradually a solution of pivaloyl chloride (11.4 ml, 0.093 mol) in dichloromethane (25 ml), followed by 1-hydroxybenzotriazole (2.0 g, 0.015 mol). To the mixture at −8±2° C. was charged in lots 3-(trifluoromethyl)-5,6,7,8-tetrahydro[1,2,4]triazolo[4,3:a]pyrazine HCl [E] (21 g, 0.092 mol) and stirring continued at 3±2° C. for 3 hours and then at 25±2° C. for 8 hours. The reaction mass was washed sequentially with water, 5% sodium hydroxide solution, again with water and then concentrated. The residue was recrystallized from 2-propanol to obtain the of titled product [F], m.p. 128° C.; Chiral Purity 100%.

$^1$H NMR (400 MHz, CDCl$_3$): δ 1.99-1.30 (m, 3H), 1.50-1.80 (m, 1H), 2.43 (dd, 1H), 2.55 (dd, 1H), 2.60-2.75 (m, 2H), 3.05-3.25 (m, 1H), 3.70-4.20 (m, 5H), 4.87 (s, 1H), 4.80-5.10 (m, 1H), 6.78-6.98 (m, 2H), 7.05 (d, 2H), 7.15-7.25 (m, 3H).

$^{13}$C NMR (200 MHz, CDCl$_3$): δ 24.88 & 25.21, 34.29, 37.47 & 38.34, 38.01 & 39.50, 42.21 & 43.00, 43.74 & 43.93, 53.25 & 53.63, 55.76 & 55.97, 105.54 (dd, $J_{C-F}$=28.9 Hz, 20.7 Hz), 119.44-119.81, 118.74 (q, $J_{C-F}$=270.9 Hz), 122.63-123.18, 126.84, 2, 128.83, 2, 127.45, 145.84 & 146.04, 150.36 & 150.95, 170.93 & 171.25.

Using similar procedure as described in Example 4, the following compounds are prepared,
(2R)-4-oxo-N-[(1R)-1-phenylethyl]-1-(2,4-difluorophenyl)-4-[3-(trifluoromethyl)-5,6-dihydro[1,2,4]triazolo[4,3-a] pyrazin-7(8H)-yl]butan-2-amine,
(2R)-4-oxo-N-[(1R)-1-phenylethyl]-1-(2,5-difluorophenyl)-4-[3-(trifluoromethyl)-5,6-dihydro[1,2,4]triazolo[4,3-a] pyrazin-7(8H)-yl]butan-2-amine,
(2R)-4-oxo-N-[(1R)-1-phenylethyl]-1-(3,4-difluorophenyl)-4-[3-(trifluoromethyl)-5,6-dihydro[1,2,4]triazolo[4,3-a] pyrazin-7(8H)-yl]butan-2-amine.

Similarly the reaction of (3R)-3-[[(1R)-1-phenylethyl] amino]-4-(2,4,5-trifluorophenyl)butanoic acid with the corresponding amines, using the procedure as described in Example 4, the following compounds are prepared,
(3R)—N-methyl-N-phenyl-3-[[(1R)-1-phenylethyl]amino]-4-(2,4,5-trifluorophenyl)-butanamide,
(3R)—N-cyclohexyl-N-methyl-3-[[(1R)-1-phenylethyl] amino]-4-(2,4,5-trifluorophenyl)butanamide,
(3R)—N-(3,5-dimethyl-1-adamantyl)-3-[[(1R)-1-phenylethyl]amino]-4-(2,4,5-trifluorophenyl)butanamide,
(3R)—N-(2-ethoxyethyl)-3-[[(1R)-1-phenylethyl]amino]-4-(2,4,5-trifluorophenyl)butanamide.

Example 5

7-[(3R)-3-Amino-1-oxo-4-(2,4,5-trifluorophenyl) butyl]-5,6,7,8-tetrahydro-3-(trifluoromethyl)-1,2,4-triazolo[4,3-a]pyrazine phosphate (Sitagliptin Phosphate)

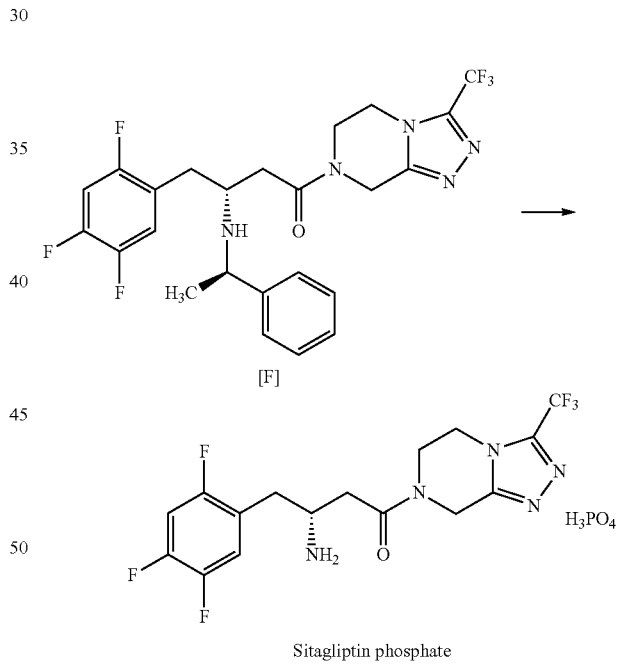

Sitagliptin phosphate (2R)-4-oxo-N-[(1R)-1-phenylethyl]-1-(2,4,5-trifluorophenyl)-4-[3-(trifluoromethyl)-5,6-dihydro[1,2,4]triazolo [4,3-a]pyrazin-7(8H)-yl]butan-2-amine [F] (25 g, 0.049 mol) was subjected to hydrogenolysis in methanol (75 ml) containing acetic acid (3.0 ml, 0.052 mol) using 5% palladium on charcoal as catalyst at 52±2° C. at hydrogen pressure of 2.0±0.5 kg/cm$^2$. After completion on reaction the catalyst was removed by filtration and reaction mass was concentrated under vacuum. Obtained residue was suspended in water and pH was set to 10.0±0.4 with solution of potassium carbonate. Product was extracted into dichloromethane. The extract was concentrated and degassed. The obtained syrupy mass was dissolved in ethanol, phosphoric acid (3.5 ml, 0.060 mol) was added and the solution refluxed for 30 min. Cooled to 5±3° C., filtered the solid and dried to obtain 20.9 g sitagliptin phosphate, chromatographic purity was 99.8%; chiral purity (determined by chiral HPLC) was 100%.

$^1$H NMR (200 MHz, DMSO-$d_6$): δ 2.70-3.10 (m, 4H), 3.50-3.75 (m, 1H), 3.85-4.35 (m, 4H), 4.80-5.05 (m, 2H), 7.46-7.67 (m, 2H).

$^{13}$C NMR (200 MHz, DMSO-$d_6$): δ 31.59, 35.06 & 35.38, 37.44 & 38.43, 41.02 & 41.66, 43.02 & 43.62, 47.58, 105.68, 119.80, 118.44, (q, $J_{C-F}$=270 Hz), 120.79-121.12, 142.53, (q, $J_{C-F}$=38 Hz), 145.84, (dd, $J_{C-F}$=239 Hz, 14 Hz), 148.34, 150.90, 156.20, (dd, $J_{C-F}$=238 Hz), 169.09 & 169.19.

Using similar procedure as described in Example 5, the following compounds are prepared,
7-[(3R)-3-amino-1-oxo-4-(2,4-difluorophenyl)butyl]-5,6,7,8-tetrahydro-3-(trifluoromethyl)-1,2,4-triazolo[4,3-a]pyrazine phosphate,
7-[(3R)-3-amino-1-oxo-4-(2,5-difluorophenyl)butyl]-5,6,7,8-tetrahydro-3-(trifluoromethyl)-1,2,4-triazolo[4,3-a]pyrazine phosphate, and
7-[(3R)-3-amino-1-oxo-4-(3,4-difluorophenyl)butyl]-5,6,7,8-tetrahydro-3-(trifluoromethyl)-1,2,4-triazolo[4,3-a]pyrazine phosphate.

Using similar procedure as described in Example 5, the following compounds are prepared as free base,
(3R)-3-amino-N-methyl-N-phenyl-4-(2,4,5-trifluorophenyl)butanamide,
(3R)-3-amino-N-cyclohexyl-N-methyl-4-(2,4,5-trifluorophenyl)butanamide,
(3R)-3-amino-N-(3,5-dimethyl-1-adamantyl)-4-(2,4,5-trifluorophenyl)butanamide,
(3R)-3-amino-N-(2-ethoxyethyl)-4-(2,4,5-trifluorophenyl)butanamide.

We claim:
1. A process for preparing a compound of formula I, or a pharmaceutically acceptable salt thereof, having the R-configuration of formula IA, or S-configuration of formula IB; selectively over the other enantiomer

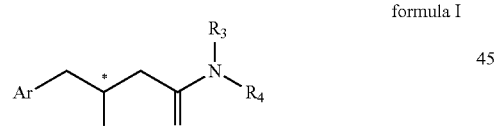

formula I

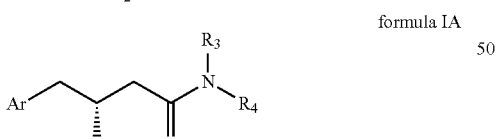

formula IA

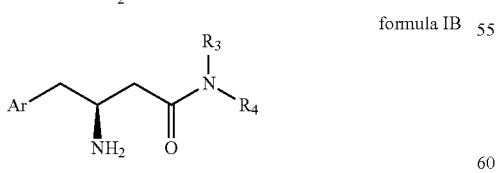

formula IB wherein,
Ar is selected from aryl or heteroaryl which is unsubstituted or substituted with one to five substituents independently selected from the group consisting of halogen, $C_{1-8}$ alkyl, hydroxyl, cyano, nitro, alkoxy, and haloalkoxy, $R_3$ and $R_4$ are each independently hydrogen, $C_{1-8}$ alkyl, aryl, or alkylaryl or arylalkyl with a proviso that it is not 1-arylalkyl; or $R_3$ and $R_4$ together with the nitrogen atom to which they are attached to form a 4- to 7-membered heterocyclic ring system optionally containing an additional heteroatom selected from O, S, N, said heterocyclic ring being unsubstituted or substituted with one to three substituents independently selected from oxo, hydroxy, halogen, $C_{1-4}$ alkoxy, and $C_{1-4}$ alkyl wherein alkyl and alkoxy are unsubstituted or substituted with one or more halogens; and said heterocyclic ring system being optionally fused with a 5 or 6-membered saturated or aromatic carbocyclic ring system or a 5 or 6-membered saturated or aromatic heterocyclic ring system containing one or two hetero atoms selected from O, S, and N, said fused ring system being unsubstituted or substituted with one or two substituents selected from hydroxy, amino, halo, $C_{1-4}$ alkyl, $C_{1-4}$ alkoxy, and haloalkyl;

comprising,
a. condensation of a compound of formula IIA, or its enantiomer of formula IIB, with a compound of formula III, or a salt thereof, to form a compound of formula IVA, or its enantiomer of formula IVB respectively;

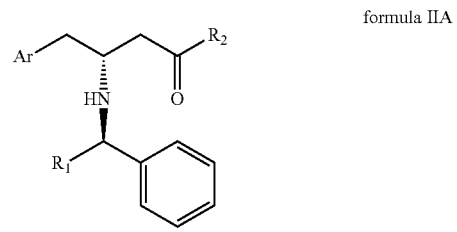

formula IIA

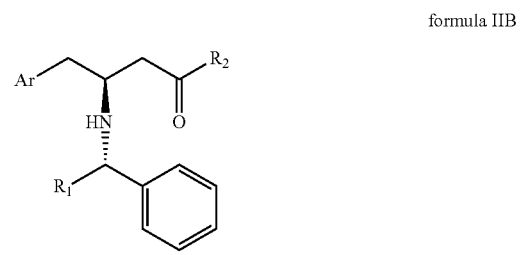

formula IIB ($R_1$ is $C_1$-$C_6$ alkyl; $R_2$ is halogen or OH)

formula III

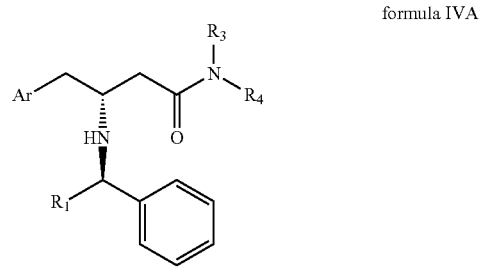

formula IVA ($R_1$ is $C_1$-$C_6$ alkyl)

formula IVB

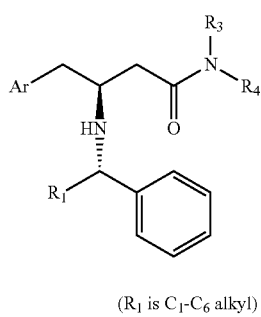

(R₁ is C₁-C₆ alkyl)

b. hydrogenolysis of the compound of formula IVA or its enantiomer a compound of formula IVB to the corresponding compound of formula IA or compound of formula IB, respectively; and
c. optionally converting the compound of formula IA or IB to a pharmaceutically acceptable salt.

2. A process for preparing a compound of formula IA-1, or a pharmaceutically acceptable salt thereof with an optical purity in excess of 99.9%, formula IA-1

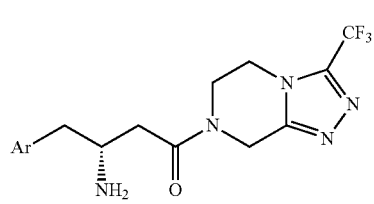

wherein Ar is unsubstituted or substituted phenyl with one to five substituents independently selected from the group consisting of halogen, $C_{1-8}$ alkyl, hydroxyl, cyano, nitro, alkoxy, and haloalkoxy; comprising, a. condensation of a compound of formula IIA-1 with 3-(trifluoromethyl)-5,6,7,8-tetrahydro[1,2,4]triazolo[4,3-[alpha]]pyrazine, a compound of formula IIA or salt thereof to form a compound of formula IVA-1;

formula IIA-1

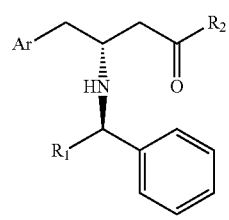

(R₁ is C₁-C₆ alkyl; R₂ is halogen or OH)

formula IIIA

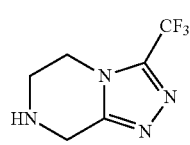

formula IVA-1

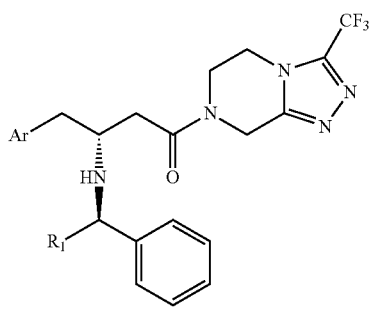

(R₁ is C₁-C₆ alkyl)

b. hydrogenolysis of the compound of formula IVA-1 to compound of formula IA-1; and
c. optionally converting the compound of formula IA-1 to a pharmaceutically acceptable salt.

3. The process as claimed in claim 1, wherein the condensation step 'a' is performed using a coupling agent selected from the group consisting of benzotriazole-1-yl-oxy-tris (dimethylamino)phosphoniumhexafluoro-phosphate (BOP), N,N'-dicyclohexylcarbodiimide (DCC), N-(3-dimethylaminopropyl)-N-ethylcarbodiimide (EDC), isobutyl chloroformate and pivaloyl chloride optionally with use of catalytic 1-hydroxybenzotriazole (HOBt), in a solvent.

4. The process as claimed in claim 3, wherein solvent is dichloromethane.

5. The process as claimed in claim 1, wherein the hydrogenolysis step 'b' is carried out using a hydrogenation catalyst in a solvent.

6. The process as claimed in claim 5, wherein the hydrogenation catalyst is palladium on charcoal and the solvent is a protic solvent selected from water, an alcohol, or a mixture thereof.

7. The process as claimed in claim 2, wherein Ar is phenyl substituted with halogen, selected from fluorine, chlorine and bromine.

8. The process as claimed in claim 7, wherein Ar is selected from 2,4,5-trifluorophenyl, 2,4-difluorophenyl 2,5-difluorophenyl, and 3,4-difluorophenyl phenyl.

9. The process as claimed in claim 2, for preparing compound of formula IA-1, wherein Ar is 2,4,5-trifluorophenyl.

10. A compound of formula IIA-1 formula IIA-1

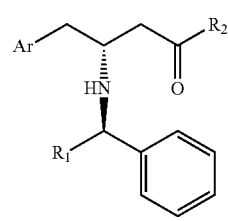

wherein, Ar is phenyl substituted with one to five halogens, selected from fluorine, chlorine and bromine; R₁ is C₁-C₆ alkyl and R₂ is OH.

11. The compound of formula IIA-1 as claimed in claim 10 wherein Ar is 2,4,5-trifluorophenyl; R₁ is methyl and R₂ is OH.

12. A process for preparing the compound of formula IIA-1, wherein Ar is 2,4,5-trifluorophenyl; $R_1$ is $C_1$-$C_6$ alkyl and $R_2$ is OH,
comprising,
  a. hydrogenating the compound of formula V in presence of a hydrogenation catalyst in a solvent to obtain a compound of formula VI, wherein R in formula V or VI is $C_1$-$C_{10}$ alkyl or cycloalkyl;

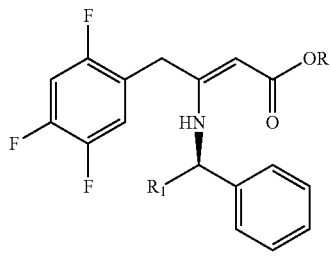

formula V

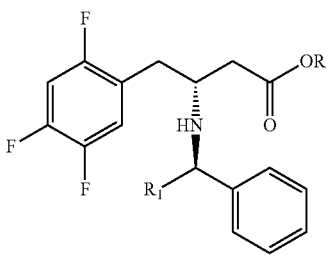

formula VI b. optionally converting the compound of formula VI to an acid addition salt; and
  c. hydrolyzing the compound of formula VI, or a salt thereof, to obtain compound of formula IIA-1, wherein $R_2$ is OH.

13. The process as claimed in claim 12, wherein the hydrogenation of compound of formula V is carried out in presence of platinum on carbon as catalyst.

14. The process as claimed in claim 12, wherein the compound of formula VI is hydrolyzed with an acid in a suitable solvent to form a crystalline salt of the compound of formula IIA-1.

15. The process as claimed in claim 12, wherein the compound is isolated as the maleate salt.

16. The process as claimed in claim 2, for preparing a compound of formula IA-1, wherein the compound is 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine phosphate.

17. The process as claimed in claim 2, for preparing a compound of formula IA-1, wherein the compound is Sitagliptin phosphate with a chiral purity of 100%.

* * * * *

UNITED STATES PATENT AND TRADEMARK OFFICE
CERTIFICATE OF CORRECTION

PATENT NO. : 8,471,016 B2  
APPLICATION NO. : 13/642872  
DATED : June 25, 2013  
INVENTOR(S) : Jadav et al.

Page 1 of 1

It is certified that error appears in the above-identified patent and that said Letters Patent is hereby corrected as shown below:

On the Title Page

In column 1, under Item "(73) Assignee", line 2, after "Andheri-East", insert --,--, therefor In the Claims In column 16, line 6, in Claim 1, delete "0," and insert --O,--, therefor In column 16, line 20, in Claim 1, after "haloalkyl;", delete "¶", therefor In column 16, line 21, in Claim 1, delete "comprising," and insert --comprising:--, therefor In column 17, line 43, in Claim 2, delete "comprising," and insert --comprising:--, therefor In column 17, line 47, in Claim 2, delete "IIA" and insert --IIIA--, therefor Signed and Sealed this  
Twenty-first Day of April, 2015

Michelle K. Lee  
*Director of the United States Patent and Trademark Office*